US010828012B2

(12) United States Patent
Morimoto

(10) Patent No.: US 10,828,012 B2
(45) Date of Patent: Nov. 10, 2020

(54) ULTRASONIC ARRAY OSCILLATOR, METHOD OF PRODUCING ULTRASONIC ARRAY OSCILLATOR, ULTRASONIC PROBE, AND ULTRASONIC DIAGNOSTIC APPARATUS

(71) Applicant: SONY CORPORATION, Tokyo (JP)

(72) Inventor: Rui Morimoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 321 days.

(21) Appl. No.: 15/752,911

(22) PCT Filed: Jun. 16, 2016

(86) PCT No.: PCT/JP2016/002905
§ 371 (c)(1),
(2) Date: Feb. 15, 2018

(87) PCT Pub. No.: WO2017/042997
PCT Pub. Date: Mar. 16, 2017

(65) Prior Publication Data
US 2018/0235574 A1    Aug. 23, 2018

(30) Foreign Application Priority Data

Sep. 7, 2015    (JP) ................. 2015-175699

(51) Int. Cl.
*A61B 8/00*     (2006.01)
*A61B 8/10*     (2006.01)
*H04R 17/00*    (2006.01)
*B06B 1/02*     (2006.01)
*B06B 1/06*     (2006.01)

(52) U.S. Cl.
CPC .............. *A61B 8/4455* (2013.01); *A61B 8/10* (2013.01); *A61B 8/4281* (2013.01); *A61B 8/4483* (2013.01); *B06B 1/0207* (2013.01); *B06B 1/0215* (2013.01); *B06B 1/0622* (2013.01); *H04R 17/00* (2013.01); *B06B 1/0269* (2013.01);
(Continued)

(58) Field of Classification Search
USPC ....................................................... 367/140
See application file for complete search history.

(56) References Cited

U.S. PATENT DOCUMENTS 5,329,498 A     7/1994  Greenstein
7,439,656 B2 *  10/2008 Ossmann .............. B06B 1/0614
                                                    310/327
(Continued)

FOREIGN PATENT DOCUMENTS

JP      06-335091 A    12/1994
JP      2003-339700 A  12/2003
(Continued)

OTHER PUBLICATIONS

European Search Report for EP 16843871 (dated Year: 2019).*
(Continued)

*Primary Examiner* — James R Hulka
(74) *Attorney, Agent, or Firm* — Chip Law Group

(57) ABSTRACT

An ultrasonic array oscillator according to the present technology includes ultrasonic oscillators and semiconductor chips. The ultrasonic oscillators form an array. The semiconductor chips are bonded to the respective ultrasonic oscillators to form impedance matching circuits.

13 Claims, 16 Drawing Sheets

(52) U.S. Cl.
 CPC ......... *B06B 1/0625* (2013.01); *B06B 2201/20* (2013.01)

(56) References Cited

U.S. PATENT DOCUMENTS

| | | | |
|---|---|---|---|
| 7,794,401 B2* | 9/2010 | Kimura | A61B 8/12 |
| | | | 310/317 |
| 10,058,891 B2* | 8/2018 | Gubbini | B06B 1/0629 |
| 2005/0146247 A1* | 7/2005 | Fisher | B06B 1/0292 |
| | | | 310/334 |
| 2006/0150380 A1* | 7/2006 | Ossmann | B06B 1/0614 |
| | | | 29/25.35 |
| 2006/0184035 A1* | 8/2006 | Kimura | A61B 8/12 |
| | | | 600/466 |

FOREIGN PATENT DOCUMENTS

| | | | |
|---|---|---|---|
| JP | 2005-087577 A | 4/2005 |
| JP | 2006-166985 A | 6/2006 |

OTHER PUBLICATIONS

International Search Report and Written Opinion of PCT Application No. PCT/JP2016/002905, dated Aug. 16, 2016, 10 pages.

\* cited by examiner

FIG. 9(a)
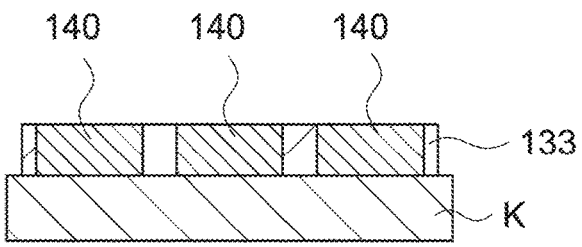
FIG. 9(b)
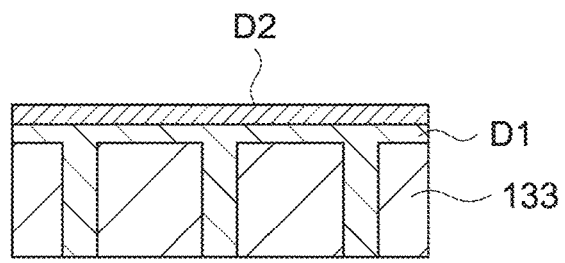
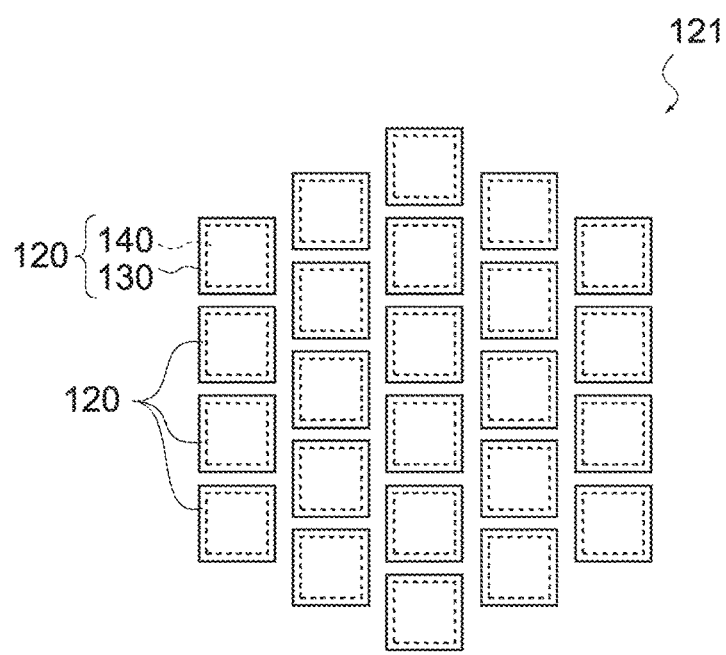
FIG.10

ULTRASONIC ARRAY OSCILLATOR, METHOD OF PRODUCING ULTRASONIC ARRAY OSCILLATOR, ULTRASONIC PROBE, AND ULTRASONIC DIAGNOSTIC APPARATUS

CROSS REFERENCE TO RELATED APPLICATIONS

This application is a U.S. National Phase of International Patent Application No. PCT/JP2016/002905 filed on Jun. 16, 2016, which claims priority benefit of Japanese Patent Application No. JP 2015-175699 filed in the Japan Patent Office on Sep. 7, 2015. Each of the above-referenced applications is hereby incorporated herein by reference in its entirety.

TECHNICAL FIELD

The present technology relates to an ultrasonic array oscillator usable for ultrasonic imaging, a method of producing an ultrasonic array oscillator, an ultrasonic probe, and an ultrasonic diagnostic apparatus.

BACKGROUND ART

An ultrasonic diagnostic apparatus widely used in a medical field and the like generates an ultrasonic image of an object to be diagnosed by irradiating the object to be diagnosed with ultrasonic waves by an ultrasonic probe and by detecting the reflected waves by the ultrasonic probe. The ultrasonic probe includes an array oscillator where a plurality of ultrasonic oscillators are arranged, and can control a convergent point of the ultrasonic waves by adjusting a delay time of driving signals input to the respective ultrasonic oscillators and detection signals output from the respective ultrasonic oscillators.

Examples of the array oscillator include a 1D array including ultrasonic oscillators arranged linearly and a 2D array including oscillators arranged on a plane. In order to improve a resolution and an imaging speed, a larger number of ultrasonic oscillators are mounted on one array oscillator. Meanwhile, ultrasonic catheters and the like inserted into blood vessels or the like are widely used. It is desirable to downsize the ultrasonic probes. Accordingly, it is desirable to densely mount the ultrasonic oscillators. Individual ultrasonic oscillators have smaller mounting areas.

Meanwhile, where the ultrasonic oscillators have the smaller mounting areas, impedance is mismatched and a detection sensitivity of the ultrasonic waves may be degraded. As a countermeasure, an amplifier is used to match the impedance. In general, an ASIC (application specific integrated circuit) is used (for example, see Patent Literature 1).

CITATION LIST

Patent Literature

Patent Literature 1: Japanese Patent Application Laid-open No. 2006-166985

DISCLOSURE OF INVENTION

Technical Problem

However, the ASIC needs a certain size. If the ASIC is mounted on each oscillator, it is difficult to secure a space to be mounted. The ASIC can be mounted apart from the oscillator. If a wiring line connecting the ASIC and the oscillator is long, the impedance matching is less effective. Moreover, the ASIC needs to be designed depending on the structure of the array oscillator and it is thus difficult to decrease production costs.

The present technology is made in view of the above-mentioned circumstances, and it is an object of the present technology to provide an ultrasonic array oscillator, a method of producing an ultrasonic array oscillator, an ultrasonic probe, and an ultrasonic diagnostic apparatus having a high impedance matching effect and excellent productivity.

Solution to Problem

In order to achieve the object, an ultrasonic array oscillator according to an embodiment of the present technology includes ultrasonic oscillators and semiconductor chips. The ultrasonic oscillators form an array. The semiconductor chips are bonded to the respective ultrasonic oscillators that form impedance matching circuits.

With this configuration, each ultrasonic oscillator and each impedance matching circuit are formed integrally, a wiring line length between the both may be short. A high impedance matching effect can be provided, an SNR (signal-noise ratio) can be improved, and the contrast of the ultrasonic image can be improved. In addition, when modules (hereinafter referred to as oscillator module) where each ultrasonic oscillator and each impedance matching circuit are formed integrally is mounted to a substrate, the modules are arranged with a high degree of freedom. Arraying and arranging the ultrasonic oscillators having different frequencies are easily optimized. Further, the oscillator modules having specific structures can be arrayed in any shapes and can correspond to a variety of apparatuses. It is possible to reuse the oscillator modules in various apparatuses. In a case where the ultrasonic oscillator has a footprint greater than that of a semiconductor chip, the same semiconductor chip can be used for any ultrasonic oscillators having any sizes.

Each of the impedance matching circuits may include an amplifier and a TR (transmit-receive) switch.

Drive signals for generating the ultrasonic waves and detection signals generated by the detection of the ultrasonic waves flow to the ultrasonic oscillators. The drive signals have signal strengths greatly different from those of the detection signals. With this configuration, only the detection signals can be amplified by switching signal paths by the TR switches and impedance matching circuits can be formed.

Each of the semiconductor chips may include a first semiconductor chip including the amplifier and a second semiconductor chip including the TR switch.

By forming the impedance matching circuits with a plurality of semiconductor chips, the size of the semiconductor chip can be reduced and it is possible to mount the impedance matching circuits to the ultrasonic oscillators having small sizes.

Each of the semiconductor chips may be an SOI (Silicon on Insulator) chip.

The SOI chip has advantages of a small size, a less leakage current, and the like, and is suitable as the semiconductor chip bonded to the ultrasonic oscillators.

The ultrasonic oscillators may include first ultrasonic oscillators each having a first frequency as a center frequency of oscillation and second ultrasonic oscillators each having a second frequency different from the first frequency as a center frequency of oscillation.

The oscillation frequencies of the ultrasonic oscillators depend on the thickness of the piezoelectric layer. By forming integrally the ultrasonic oscillators and the impedance matching circuits, the ultrasonic oscillators having greatly different oscillation frequencies can be arranged with a high degree of freedom.

The ultrasonic array oscillators may further include MEMS (Micro Electro Mechanical Systems). The MEMS and the ultrasonic oscillators form the array.

By arraying the ultrasonic oscillators and the MEMS, the ultrasonic waves can be generated by using the ultrasonic oscillators having great ultrasonic strength, and the reflected waves can be detected by using the MEMS module having high sensitivity. Thus, it is possible to improve a detection sensitivity.

The ultrasonic array oscillator may further includes optical devices, the optical devices and the ultrasonic oscillators forming the array.

By arraying the ultrasonic oscillators and the optical devices, it is possible to perform light ultrasonic imaging with a single ultrasonic probe. The ultrasonic imaging detects the ultrasonic waves generated by the light irradiated from the optical devices.

In order to achieve the object, a method of producing an ultrasonic array oscillator according to an embodiment of the present technology includes mounting ultrasonic oscillators, to which semiconductor chips that form impedance matching circuits are bonded, by using a pick-and-place method.

The ultrasonic oscillators may include first ultrasonic oscillators each having a first frequency as a center frequency of oscillation and second ultrasonic oscillators each having a second frequency different from the first frequency as a center frequency of oscillation.

In the method of producing the ultrasonic array oscillator, the mounting step includes mounting the ultrasonic oscillators and the MEMS by using the pick-and-place method.

In the method of producing the ultrasonic array oscillator, the mounting step includes mounting the ultrasonic oscillators and optical devices by using the pick-and-place method.

In order to achieve the object, an ultrasonic probe according to an embodiment of the present technology includes an ultrasonic array oscillator.

The ultrasonic array oscillator includes ultrasonic oscillators that form an array, and semiconductor chips bonded to respective of the ultrasonic oscillators that form impedance matching circuits.

In order to achieve the object, an ultrasonic diagnostic apparatus according to an embodiment of the present technology includes an ultrasonic probe and a main body.

The ultrasonic probe includes an ultrasonic array oscillator, the ultrasonic array oscillator including ultrasonic oscillators that form an array, and semiconductor chips bonded to respective of the ultrasonic oscillators that form impedance matching circuits The main body to which the ultrasonic probe is connected, the main body supplying the ultrasonic array oscillator with a drive signal and generating an ultrasonic image on the basis of a detection signal output from the ultrasonic array oscillator.

Advantageous Effects of Invention

As described above, the present technology can provide an ultrasonic array oscillator, a method of producing an ultrasonic array oscillator, an ultrasonic probe, and an ultrasonic diagnostic apparatus having a high impedance matching effect and excellent productivity. It should be noted that the effects described here are not necessarily limitative and may be any of effects described in the present disclosure.

BRIEF DESCRIPTION OF DRAWINGS

FIGS. 9(a) and 9(b) are schematic views showing a method of producing the ultrasonic array oscillator.

FIG. 10 is a schematic view showing an arrangement of the oscillator modules included in the ultrasonic array oscillator.

MODE(S) FOR CARRYING OUT THE INVENTION

[Configuration of Ultrasonic Diagnostic Apparatus]

Figure 1:
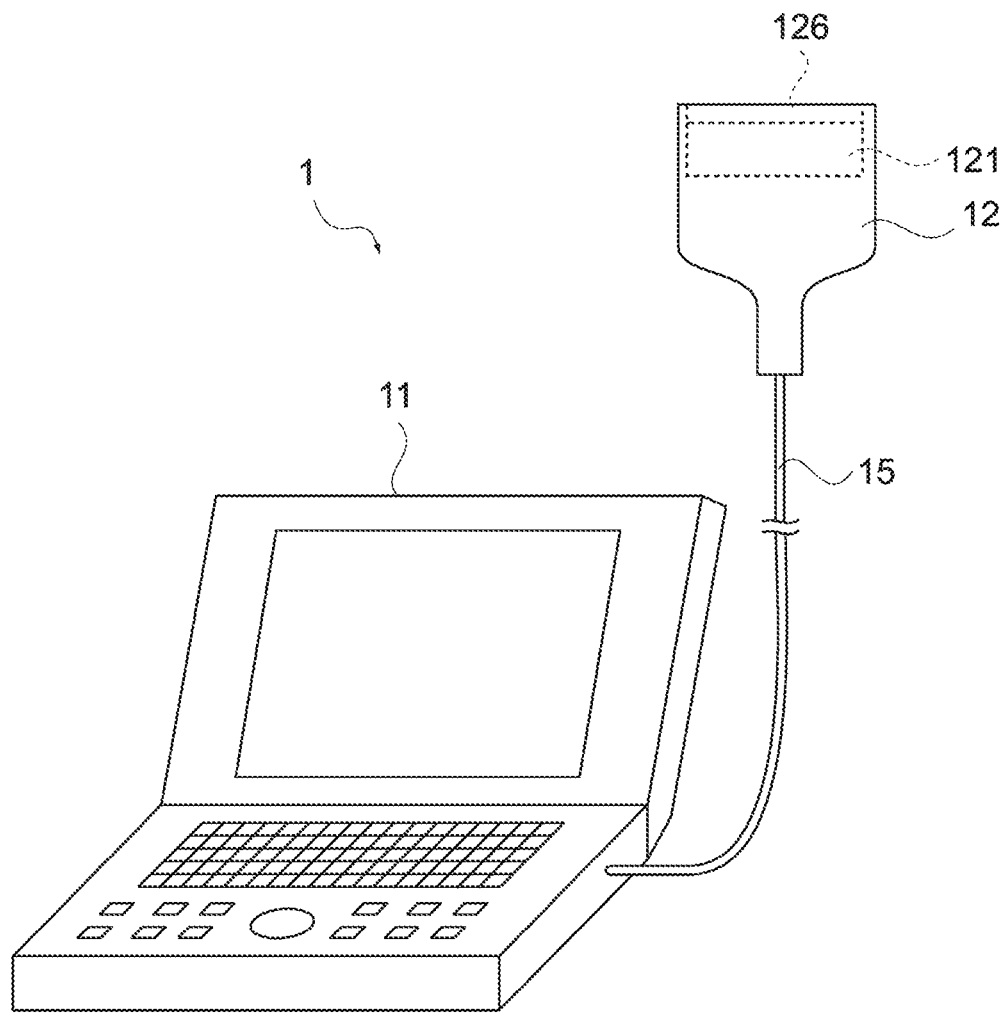
FIG. 1 is a schematic view showing a configuration of an ultrasonic diagnostic apparatus according to this embodiment.

FIG. 1 is a schematic view showing a configuration of an ultrasonic diagnostic apparatus 1 according to this embodiment. As shown in FIG. 1, the ultrasonic diagnostic apparatus 1 includes a main body 11, an ultrasonic probe 12, and a cable 15. The main body 11 is connected to the ultrasonic probe 12 via the cable 15.

The main body 11 supplies the ultrasonic probe 12 with drive signals via the cable 15, generates an ultrasonic image on the basis of ultrasonic wave detection signals output from the ultrasonic probe 12, and displays the ultrasonic image on the display.

The ultrasonic probe 12 includes an array oscillator 121, comes in contact with an object to be diagnosed, emits an ultrasonic wave, and detects reflected waves. The ultrasonic probe 12 is supplied with the drive signals from the main body 11 via the cable 15, and outputs the detection signals to the main body 11.

Types of the ultrasonic probe 12 are not especially limited. Any type of the ultrasonic probe, e.g., a linear type, sector type, convex type, or radial type ultrasonic probe, may be used. A two-dimensional array type ultrasonic probe may be used. Alternatively, the ultrasonic probe 12 may be an ultrasonic catheter that can be inserted into blood vessels and the like.

[Configuration of Array Oscillator]

Figure 2:
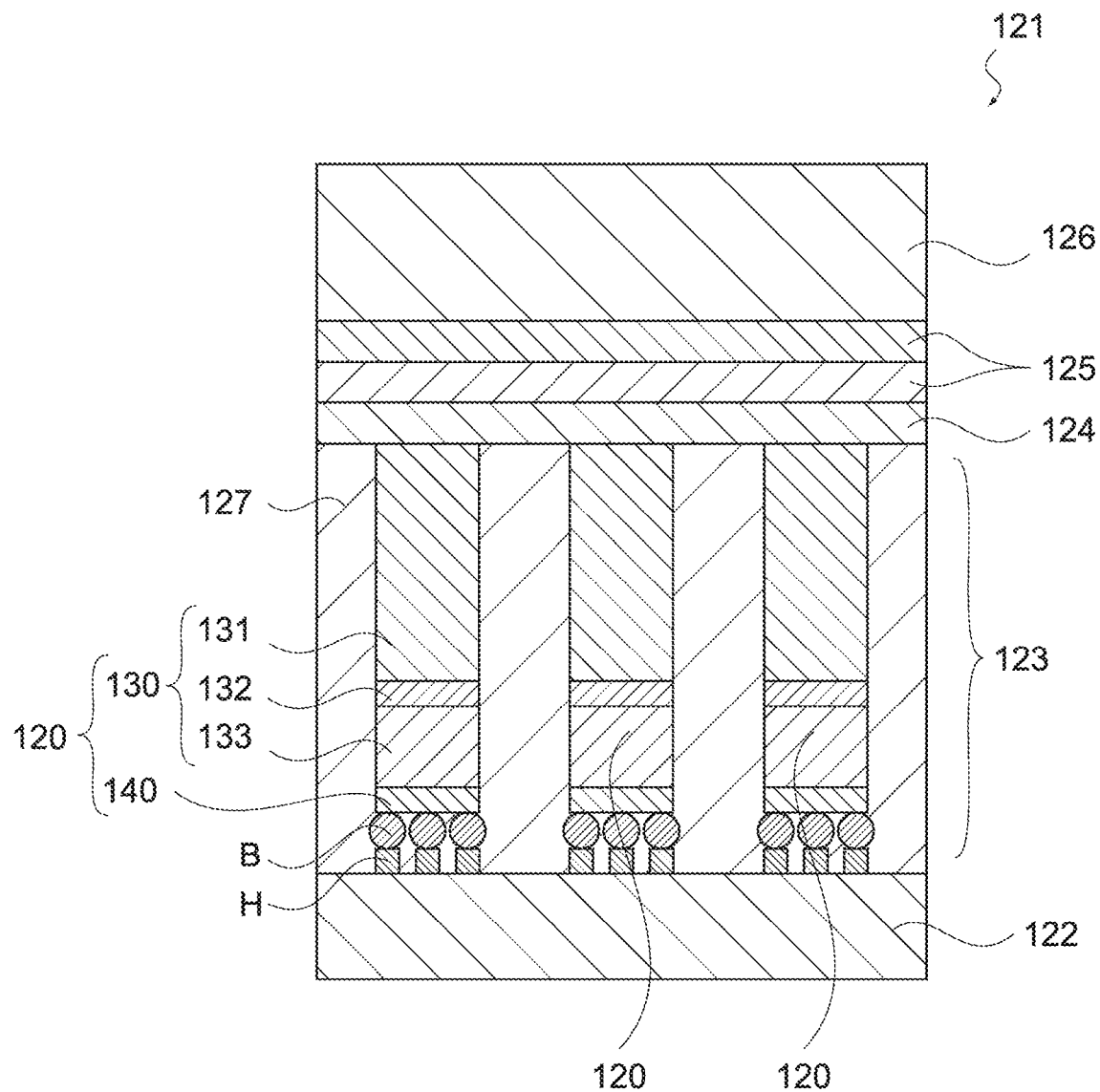
FIG. 2 is a cross-sectional view showing the structure of an ultrasonic array oscillator included in the ultrasonic diagnostic apparatus.

FIG. 2 is a cross-sectional view showing the structure of the array oscillator 121. As shown in FIG. 2, the array oscillator 121 includes a substrate 122, an oscillator layer 123, an upper electrode layer 124, acoustic matching layers 125, and an acoustic lens 126. They are laminated in an order of the substrate 122, the oscillator layer 123, the upper electrode layer 124, the acoustic matching layers 125, and the acoustic lens 126.

The substrate 122 is a rigid print substrate, an FPC (flexible printed circuits) substrate, or the like. Wiring lines H and bumps B are formed on the mounting surface. The wiring lines H are connected to the main body 11 via the cable 15.

The oscillator layer 123 includes a plurality of oscillator modules 120 and a filler 127. Each of the plurality of oscillator modules 120 is mounted to the substrate 122 via the bumps B. The filler 127 is filled between the respective oscillator modules 120. The filler 127 may be acrylic resin, polyurethane resin, or an acoustic absorber. The oscillator modules 120 will be described later in detail.

Note that while only three oscillator modules 120 are shown in FIG. 2, the array oscillator 121 in fact includes a larger number of (from about several hundreds to about several thousands) oscillator modules 120.

The upper electrode layer 124 functions as an electrode of piezoelectric layers 131 as described later. The upper electrode layer 124 is formed of an electric conductive material, e.g., metal plating. Note that the upper electrode layer 124 may be formed over the plurality of oscillator modules 120 as shown in FIG. 2, or may be separated for each of the oscillator modules 120.

The acoustic matching layers 125 decrease an acoustic impedance difference between the object to be diagnosed and the ultrasonic oscillators 130, and prevents ultrasonic waves from reflecting toward the object to be diagnosed. The acoustic matching layers 125 are formed of synthetic resin or a ceramics material. The number of the acoustic matching layers 125 may be two as shown in FIG. 2. Alternatively, one acoustic matching layer or three or more acoustic matching layers may be used.

The acoustic lens 126 converges the ultrasonic waves generated by the oscillator layer 123. The acoustic lens 126 is positioned at a tip of the ultrasonic probe 12 as shown in FIG. 1, and comes in contact with the object to be diagnosed. The acoustic lens 126 is formed of silicone rubber or the like, and its size and shape are not especially limited.

[Configuration of Oscillator Module]

Figure 3:
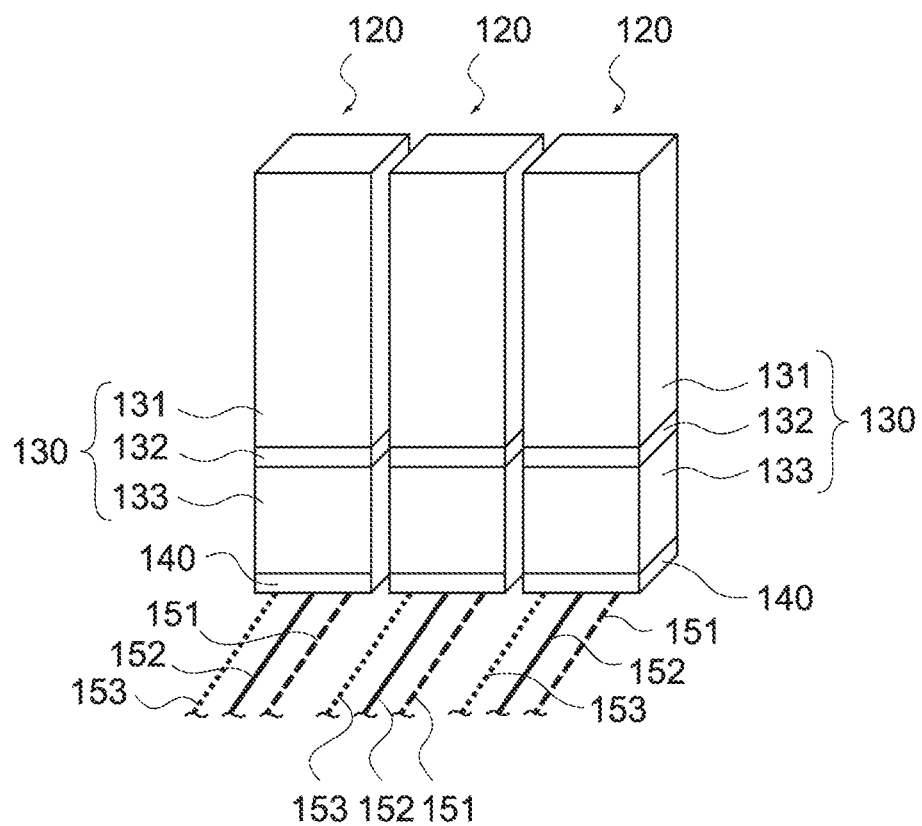
FIG. 3 is a perspective view showing the oscillator modules included in the ultrasonic array oscillator.

FIG. 3 is a schematic view showing the oscillator modules 120. As shown in FIG. 3, each oscillator module 120 includes an ultrasonic oscillator 130 and a circuit chip 140. A power supply wiring line 151, a signal wiring line 152, and a ground wiring line 153 are connected to each oscillator module 120.

Each ultrasonic oscillator 130 includes a piezoelectric layer 131, a lower electrode layer 132, and a backing layer 133. These are laminated in an order of the backing layer 133, the lower electrode layer 132, and the piezoelectric layer 131.

The piezoelectric layer 131 is formed of a piezoelectric material such as PZT (lead zirconate titanate). When a voltage is applied between the lower electrode layer 132 and the upper electrode layer 124 (see FIG. 2), the piezoelectric layer 131 generates vibration due to an inverse piezoelectric effect, and generates the ultrasonic waves. In addition, when the reflected waves from the object to be diagnosed enter the piezoelectric layer 131, polarization is generated due to a piezoelectric effect. The size of the piezoelectric layer 131 is not especially limited, but may be 250 μm square, for example.

The lower electrode layer 132 functions as an electrode of the piezoelectric layer 131. The lower electrode layer 132 is formed of an electric conductive material, e.g., metal plating.

The backing layer 133 is laminated on the circuit chip 140, and absorbs unnecessary vibration of the ultrasonic oscillator 130. The backing layer 133 is formed of a material such as a mixture of a filler and synthetic resin.

The circuit chip 140 is bonded to each ultrasonic oscillator 130, and forms an impedance matching circuit of the ultrasonic oscillator 130. The circuit chip 140 is a semiconductor chip formed of a semiconductor material. Specifically, the circuit chip 140 can be an SOI chip produced by an SOI (Silicon on Insulator) process. More specifically, the circuit chip 140 can be a BGD-SOI chip produced by a BCD-SOI (bipolar CMOS DMOS) process.

Each circuit chip 140 may be bonded to each ultrasonic oscillator 130, and may not necessarily be arranged between the backing layer 133 and the substrate 122. Also, the circuit chips 140 may not be bonded to all the ultrasonic oscillators 130, and may be bonded only some of the ultrasonic oscillators 130. The size of the circuit chip 140 can be the same as or smaller than the size of the bottom surface of the ultrasonic oscillator 130.

Figure 4:
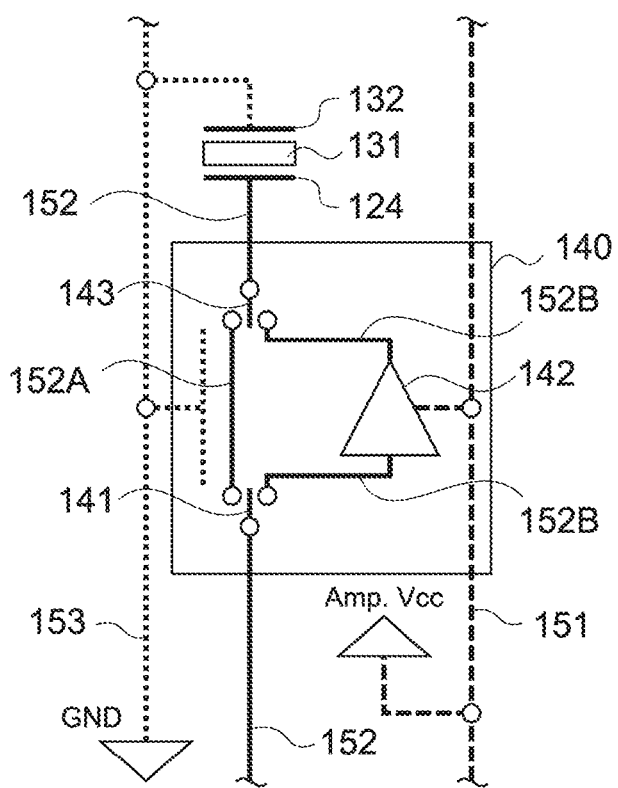
FIG. 4 is a schematic view showing a circuit configuration of the oscillator modules included in the ultrasonic array oscillator.

FIG. 4 is a schematic view showing a circuit configuration of the circuit chip 140. As shown in FIG. 4, the circuit chip 140 includes a first TR (transmit-receive) switch 141, an amplifier 142, and a second TR switch 143.

The power supply wiring line 151 is connected to the amplifier 142. The signal wiring line 152 is connected to the upper electrode layer 124, and is separated into a signal wiring line 152A not via the amplifier 142 and a signal wiring line 152B via the amplifier 142. The ground wiring line 153 is connected to the lower electrode layer 132.

The first TR switch 141 is connected to the signal wiring line 152, and switches a signal path between the signal wiring line 152A and the signal wiring line 152B. The first TR switch 141 can be a transistor or a diode.

The amplifier 142 is connected to the signal wiring line 152B, and amplifies signals flowing through the signal wiring line 152B by utilizing electric power supplied from the power supply wiring line 151. The amplifier 142 can be a diode.

The second TR switch 143 is connected to the signal wiring line 152, and switches a signal path between the signal wiring line 152A and the signal wiring line 152B. The second TR switch 143 can be a transistor or a diode.

The oscillator module 120 has the above-described configuration. As described above, since each oscillator module 120 includes the circuit chip 140 that forms an impedance matching circuit, a wiring line length between the ultrasonic oscillator and the impedance matching circuit is short, and an impedance matching is effectively performed. This allows an SNR (signal-noise ratio) to be improved, and the contrast of the ultrasonic image to be increased.

[Operation of Ultrasonic Diagnostic Apparatus]

An operation of the ultrasonic diagnostic apparatus 1 will be described. When the ultrasonic diagnostic apparatus 1 is turned on, the ultrasonic probe 12 is supplied with electric power from the main body 11 via the cable 15 (see FIG. 1). The electric power flows to the power supply wiring line 151 via the substrate 122 and is supplied to the amplifier 142 (see FIG. 4).

When the ultrasonic probe 12 comes in contact with the object to be diagnosed and an instruction to start diagnosis is input, the main body 11 generates the drive signals. The drive signals are supplied to the ultrasonic probe 12 via the cable 15, and flow to the signal wiring line 152 via the substrate 122. In this case, the first TR switch 141 and the second TR switch 143 are switched to a signal wiring line 152A side, and the drive signals are supplied to the upper electrode layer 124 via the second TR switch 143 and the first TR switch 141.

Due to a potential difference between the upper electrode layer 124 and the lower electrode layer 132, the piezoelectric layer 131 generates vibration due to an inverse piezoelectric effect, and generates the ultrasonic waves. The generated ultrasonic waves enter the object to be diagnosed via the acoustic matching layer 125 and the acoustic lens 126.

The reflected waves generated in the object to be diagnosed enter the piezoelectric layer 131 via the acoustic lens 126 and the acoustic matching layer 125. The piezoelectric layer 131 is polarized due to the piezoelectric effect, and a current (hereinafter referred to as detection signals) flows through the signal wiring line 152. In this case, the first TR switch 141 and the second TR switch 143 are switched to a signal wiring line 152B side, and the detection signals are amplified by the amplifier 142. The amplified detection signals flow from the first TR switch 141 to the signal wiring line 152 and are transmitted to the main body 11 via the substrate 122 and the cable 15.

The main body 11 generates the ultrasonic image on the basis of the detection signals. As described above, the drive signals are transmitted to the upper electrode layer 124 not via the amplifier 142, but the detection signals are amplified by the amplifier 142 and are transmitted to the main body 11. The route switching of the drive signal and the detection signal is performed by the first TR switch 141 and the second TR switch 143. Thus, the impedances between the drive signals having a great signal strength and the detection signal having a small signal strength can be matched.

[Method of Producing Array Oscillator]

FIGS. 5(a), 5(b), 5(c), 6(a), 6(b), 6(c), 7(a), 7(b), 7(c), 8(a), 8(b), and 8(c) are schematic views showing a method of producing the array oscillator 121. As shown in FIG. 5 (a), the circuit chips 140 are arranged on a sacrifice substrate K. The circuit chips 140 can be adhered to the sacrifice substrate K with an adhesive that is peeled by UV (ultraviolet) irradiation.

Figure 5A:
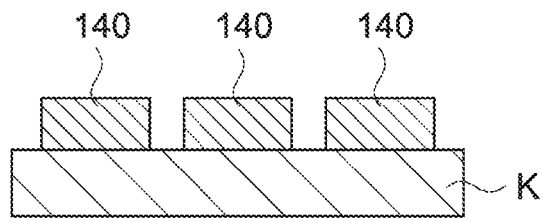
FIGS. 5(a), 5(b), and 5(c) are schematic views showing a method of producing the ultrasonic array oscillator.
Figure 5B:
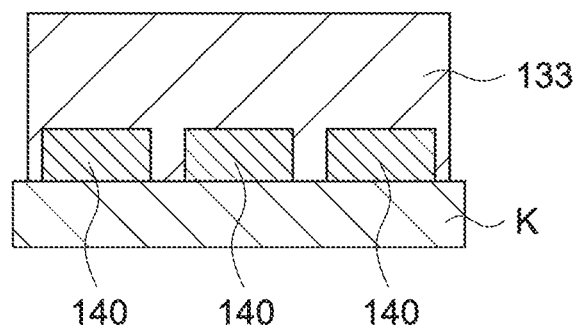
Figure 5C:
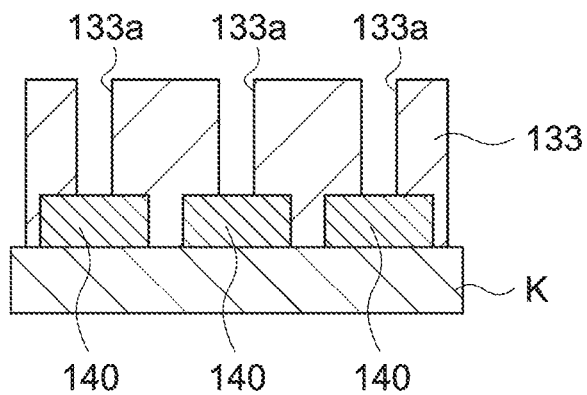

Next, as shown in FIG. 5(b), the backing layer 133 is laminated on the sacrifice substrate K and the circuit chips 140. Next, as shown in FIG. 5(c), parts of the backing layer 133 are removed to expose the circuit chips 140. Openings 133a are formed by the removal.

Figure 6A:
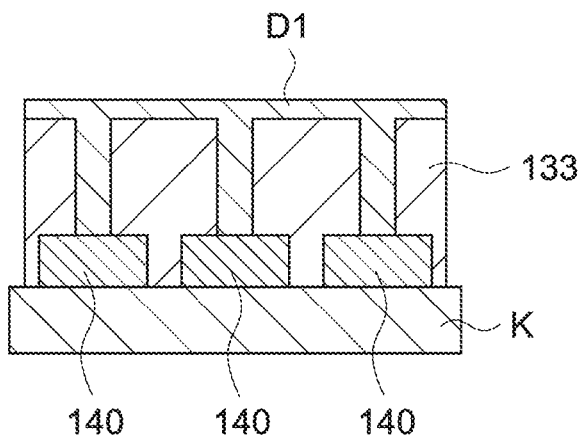
FIGS. 6(a), 6(b), and 6(c) are schematic views showing a method of producing the ultrasonic array oscillator.
Figure 6B:
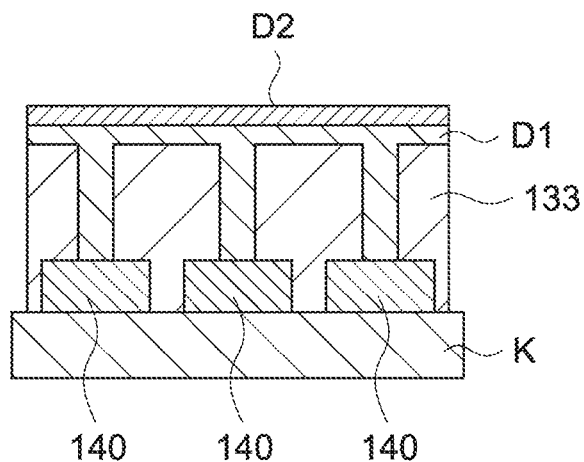

Next, as shown in FIG. 6(a), a conductive material D1 is arranged in the openings 133a and over the backing layer 133. The conductive material D1 includes metal such as copper, for example. Next, as shown in FIG. 6(b), a conductive material D2 is arranged on the conductive material D1. The conductive material D2 can be a conductive adhesive. The conductive material D1 and the conductive material D2 form the lower electrode layer 132.

Figure 6C:
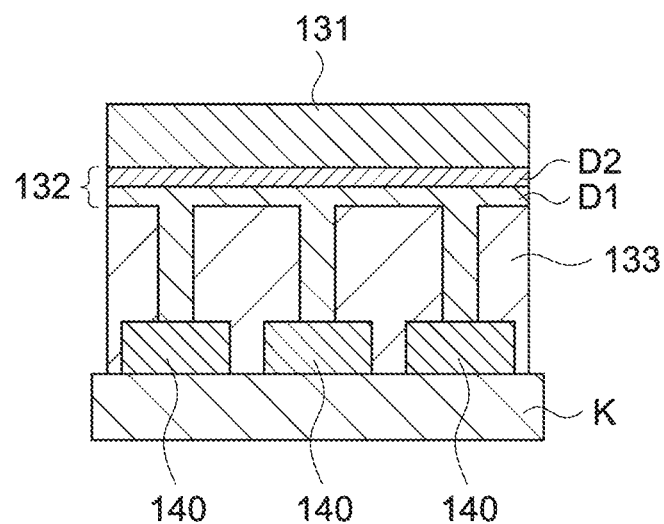
Figure 7A:
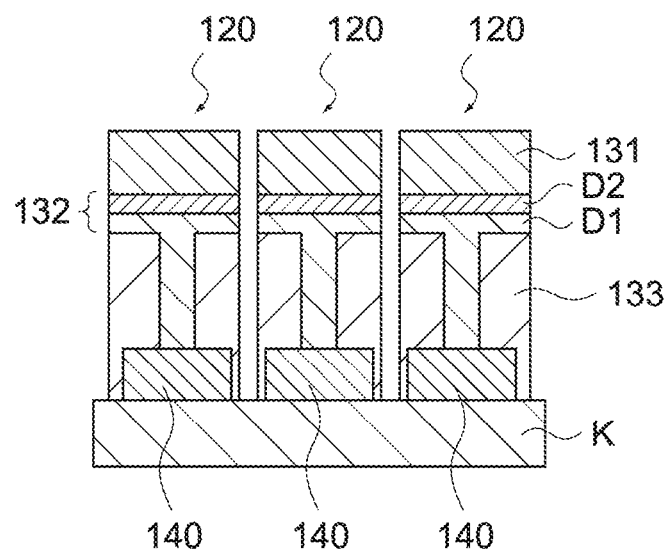
FIGS. 7(a), 7(b), and 7(c) are schematic views showing a method of producing the ultrasonic array oscillator.

Next, as shown in FIG. 6(c), the piezoelectric layer 131 is arranged on the conductive material D2 and adhered by the conductive material D2. Next, as shown in FIG. 7(a), the piezoelectric layer 131 and the backing layer 133 are cut by dicing to separate into individual oscillator modules 120.

Figure 7B:
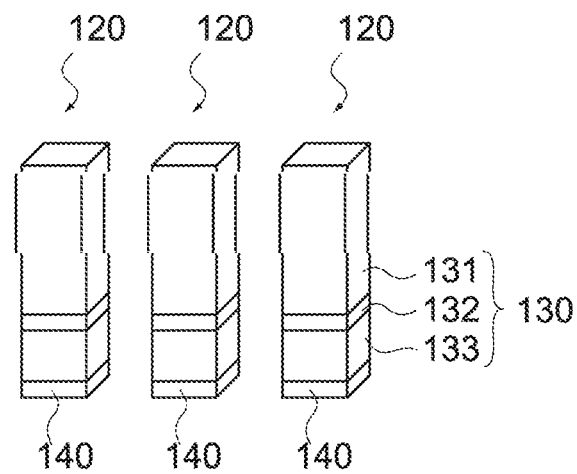

Next, the oscillator modules 120 are separated from the sacrifice substrate K. By ultraviolet irradiation, the adhesive between the circuit chip 140 and the sacrifice substrate K can be peeled. FIG. 7(b) is a schematic view showing the oscillator modules 120 separated from the sacrifice substrate K.

Figure 7C:
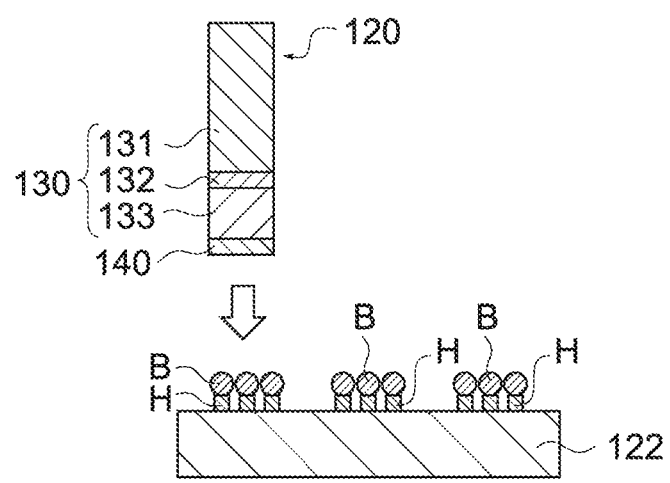

Next, as shown in FIG. 7(c), the oscillator module 120 is mounted to the substrate 122. As shown in FIG. 7(c), the wiring lines H and the bumps B are formed on the substrate 122. Note that the wiring lines H are the power supply wiring line 151, the signal wiring line 152, and the ground wiring line 153. The oscillator module 120 can be mounted to the substrate 122 by connecting the circuit chip 140 to the wiring lines H via the bumps B.

Figure 8A:
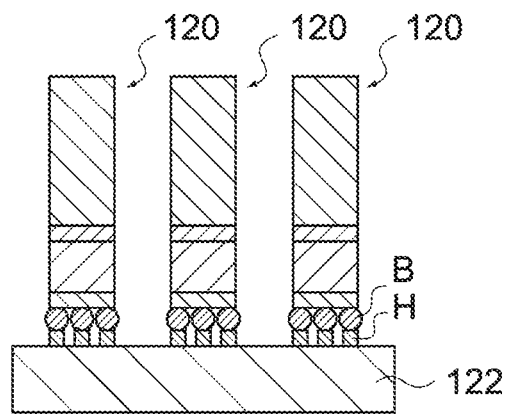
FIGS. 8(a), 8(b), and 8(c) are schematic views showing a method of producing the ultrasonic array oscillator.

Next, as shown in FIG. 8(a), other oscillator modules 120 are mounted to the substrate 122, respectively. Note that a method of mounting objects to be mounted separately in this way is called as a pick-and-place method.

Figure 8B:
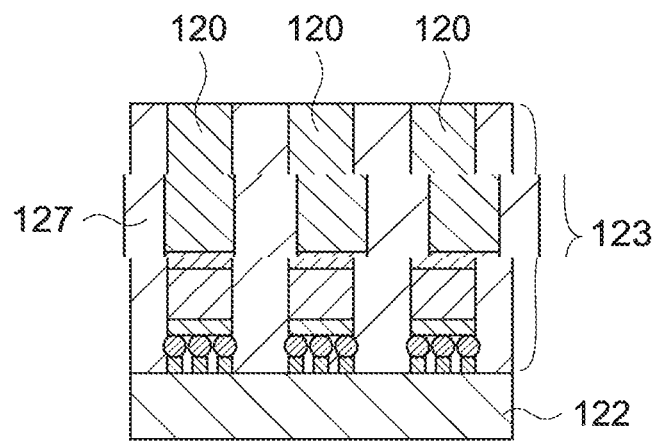
Figure 8C:
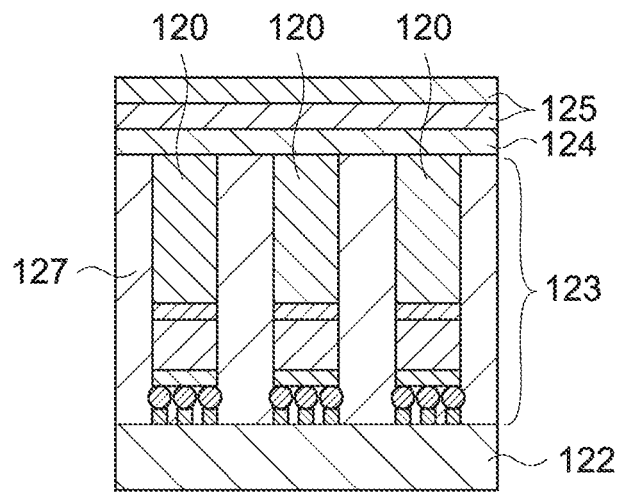

Next, as shown in FIG. 8(b), the filler 127 is filled between the respective oscillator modules 120 to form the oscillator layer 123. Next, as shown in FIG. 8(c), the upper electrode layer 124 and the acoustic matching layer 125 are laminated on the oscillator layer 123.

Next, the acoustic lens 126 is laminated on the acoustic matching layer 125 (see FIG. 2). In the above-described manner, the array oscillator 121 can be produced. As described above, in the array oscillator 121 according to this embodiment, since each ultrasonic oscillator 130 and each circuit chip 140 are formed integrally, the pick-and-place method can be used for mounting.

Here, the array oscillator used for the ultrasonic diagnostic apparatus includes about several thousands of ultrasonic oscillators. In particular, a medical ultrasonic probe has a different configuration depending on each diagnosis item. Even if the pick-and-place method is used, the costs are not high.

In addition, in the related art, it is necessary to produce array oscillators separately for a variety of ultrasonic probes including array oscillators having different shapes. In contrast, according to this embodiment, the oscillator modules 120 can be freely arranged by the pick-and-place method.

Thus, it is possible to use the oscillator modules 120 having the same structure in a variety of the ultrasonic probes.

Note that the method of producing the array oscillator 121 is not limited to the above-described method. FIGS. 9(a) and 9(b) are schematic views showing another method of producing the array oscillator 121. As shown in FIG. 5 (a), the circuit chips 140 are arranged on the sacrifice substrate K. Thereafter, as shown in FIG. 9 (a), the backing layer 133 is formed in a thickness similar to the thickness of the circuit chips 140.

Further, as shown in FIG. 9(b), a structure, in which the backing layer 133, the conductive material D1, and the conductive material D2 are laminated, is produced. By laminating the laminate on the structure of FIG. 9(a), the structure of FIG. 6(b) can be produced. The array oscillator 121 can be produced by the method similar to the above-described method after that.

[Arrangement of Oscillator Modules]

As described above, the ultrasonic probe 12 according to this embodiment includes the oscillator modules 120 each having the ultrasonic oscillator 130 and the circuit chip 140, and the oscillator modules 120 can be mounted to the substrate 122 one by one. Accordingly, oscillator modules 120 can be arranged with a high degree of freedom.

FIG. 10 is a schematic view showing an arrangement of the oscillator modules 120, which are viewed from the direction perpendicular to the substrate 122 (see FIG. 2). As shown in FIG. 10, the oscillator modules 120 can have a honeycomb 2D arrangement. The honeycomb 2D arrangement refers to a regular hexagon provided by lines connecting the centers of the oscillator modules 120 viewed from the direction perpendicular to the substrate 122.

In general, it is desirable for an ultrasonic probe to decrease a side lobe (ultrasonic waves emitted in the directions deviated from the center direction which is directed by the ultrasonic waves). The honeycomb 2D arrangement can widen the spaces between the adjacent ultrasonic oscillators 130, and can suppress the side lobe.

In particular, by the Dice and Fill method used for the production of the array oscillator in the related art, large electrodes in a honeycomb 2D arrangement are arranged on piezoelectric devices diced small in a lattice. This method results in a substantial degraded device pitch width. In contrast, in the array oscillator 121 according to this embodiment, it is possible to arrange the ultrasonic oscillators 130 at minimum device processing pitches by the pick-and-place method.

Figure 11:
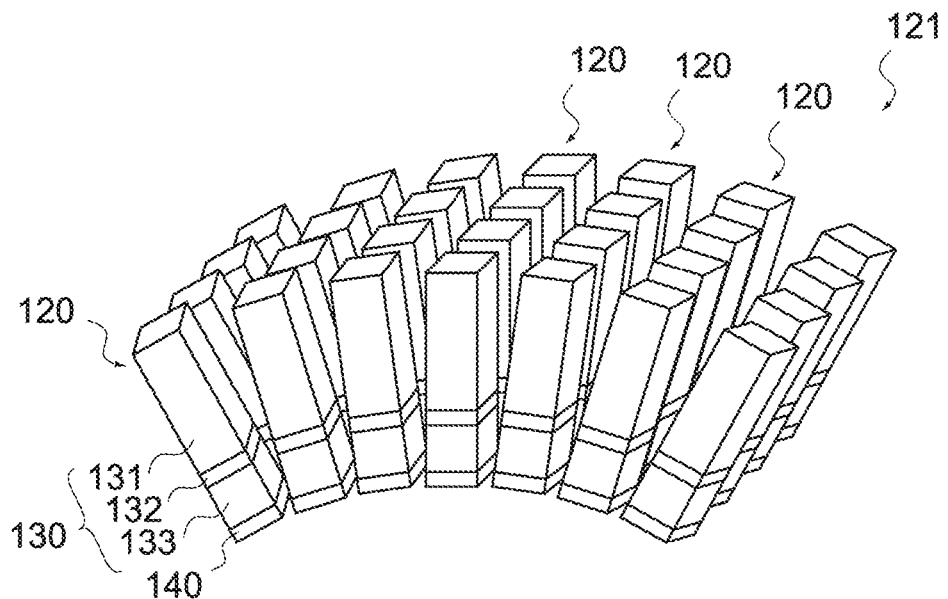
FIG. 11 is a schematic view showing a convex type ultrasonic probe of the oscillator modules included in the ultrasonic array oscillator.

FIG. 11 is a schematic view showing a convex type ultrasonic probe including the oscillator modules 120 according to this embodiment. As shown in FIG. 11, it is necessary to arrange the oscillator modules 120 on a curved surface in the convex type ultrasonic probe. However, the impedance matching circuits in the related-art structure are provided by the ASICs, it is difficult to arrange the ASICs on the curved surface.

In contrast, the array oscillator 121 according to this embodiment includes the oscillator modules 120 each including the ultrasonic oscillator 130 and the circuit chip 140 integrally formed. As shown in FIG. 11, the oscillator modules 120 can be densely mounted. Thus, it is possible to improve a contrast of the ultrasonic image and a slice resolution (resolution in a depth direction of the object to be diagnosed).

Figure 12:
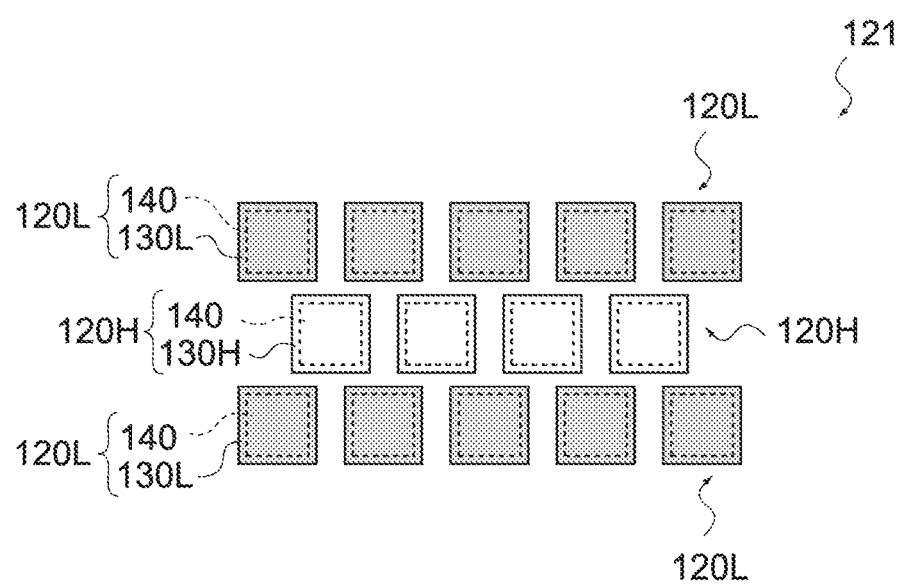
FIG. 12 is a schematic view showing a Hanafy lens type ultrasonic probe of the oscillator modules included in the ultrasonic array oscillator.

FIG. 12 is a schematic view showing a Hanafy lens type ultrasonic probe including the oscillator modules 120 according to this embodiment. The Hanafy lens uses two or more types of ultrasonic oscillators as the array oscillator in order to improve the slice resolution.

As shown in FIG. 12, the array oscillator 121 includes oscillator modules 120L each including an ultrasonic oscillator 130L having a low center frequency of oscillation (large opening size) and an oscillator modules 120H each including ultrasonic oscillator 130H each having a high center frequency of oscillation (small opening size). Note that as the frequency of each ultrasonic oscillator 130 is determined by the thickness of each piezoelectric layer 131, the thickness of the piezoelectric layer 131 of each ultrasonic oscillator 130L is different from the thickness of the piezoelectric layer 131 of each ultrasonic oscillator 130.

The Hanafy lens allows an ultrasonic beam diameter to be uniform in the depth direction by changing focal points of the ultrasonic waves at an inner periphery side and at an outer periphery side. As described above, since the frequency of each ultrasonic oscillators is determined by the thickness of the piezoelectric layer, the array oscillator has been produced in the related art by curving that the piezoelectric layer is machined to have a curved surface and dicing that the piezoelectric layer is divided. In contrast, according to this embodiment, the ultrasonic oscillators 130 including the piezoelectric layers 131 with different thicknesses are produced in advance, and can be mounted separately by using the pick-and-place method.

Thus, it is possible to produce the array oscillator 121 including the ultrasonic oscillators 130L and the ultrasonic oscillators 130H with a greater frequency difference therebetween as compared with an array oscillator produced by the curving. Also, it is possible to freely decide the arrangement of the ultrasonic oscillators 130L and the ultrasonic oscillators 130H. Furthermore, the Hanafy lens can have the honeycomb 2D arrangement, and the side lobe can be decreased.

[Arrangement and Number of Circuit Chips]

As described above, each oscillator module 120 of the array oscillator 121 includes the ultrasonic oscillator 130 and the circuit chip 140. Here, not one circuit chip 140 but a plurality of the circuit chips 140 may be used.

Figure 13:
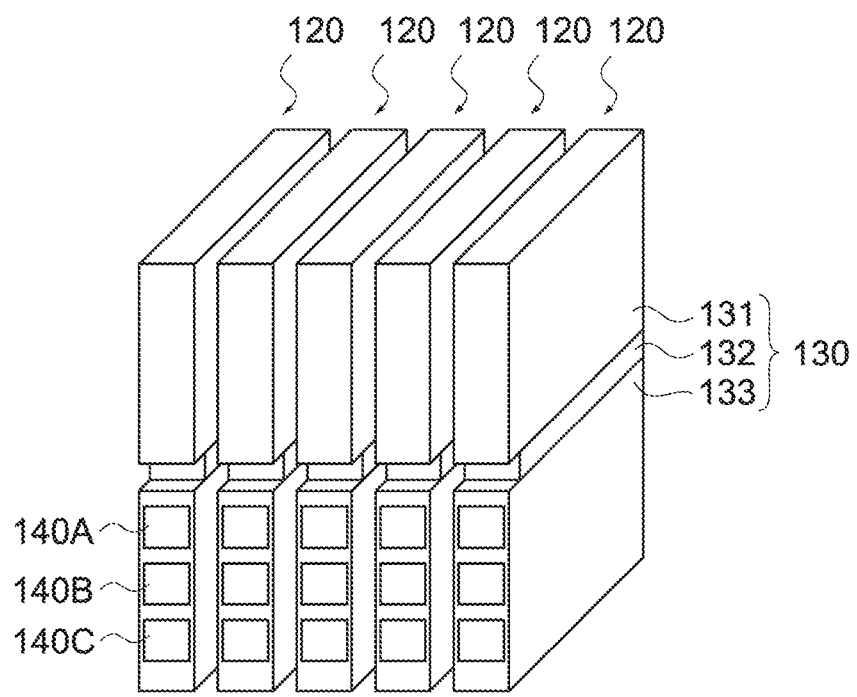
FIG. 13 is a schematic view showing a 1D arrangement array of the oscillator modules included in the ultrasonic array oscillator.

FIG. 13 is a schematic view showing the array oscillator 121 including the oscillator modules 120 having a plurality of circuit chips. As shown in FIG. 13, the array oscillator 121 can be a narrow chip 1D arrangement array including narrow ultrasonic oscillators 130 arranged in one direction. The circuit chips 140 can include three circuit chips, i.e., the circuit chip 140A, the circuit chip 140B, and circuit chip 140C.

Figure 14:
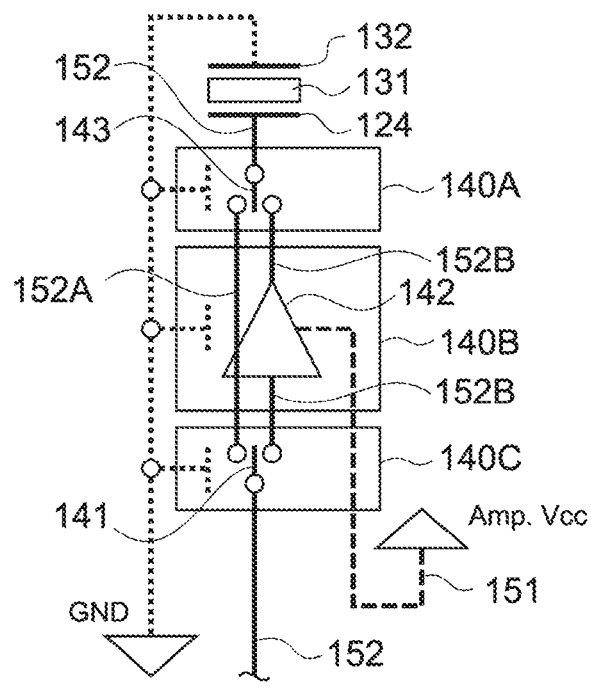
FIG. 14 is a schematic view showing circuit configurations of the oscillator modules included in the ultrasonic array oscillator.

FIG. 14 is a schematic view showing circuit configurations of the circuit chips 140A to C. As shown in FIG. 14, the circuit chip 140A includes the second TR switch 143, the circuit chip 140B includes the amplifier 142, and the circuit chip 140C includes the first TR switch 141, respectively. The first TR switch 141, the amplifier 142, and the second TR switch 143 operate as described above. The circuit chips 140A to C may be produced by dicing and cutting the circuit chips 140, or may be separately produced.

When the circuit chip 140 is divided into devices of the impedance matching circuit, the circuit chips 140 can be downsized. Even if the widths of the ultrasonic oscillators 130 are narrow like the narrow pith 1D arrangement array, it is possible to bond the circuit chips 140 to the ultrasonic oscillators 130. Note that the circuit chip 140 may include two circuit chips. For example, one circuit chip has the amplifier 142 and the other circuit chip has the first TR switch 141 and the second TR switch 143.

[Application to IVUS]

An IVUS (intravascular ultrasonic endoscope) is one type of the ultrasonic probes, and is used for observation of vascular walls of coronary blood vessels. The IVUS includes an array oscillator having a plurality of ultrasonic oscillators arranged circumferentially and an amplifier that amplifies detection signals output from respective ultrasonic oscillators.

Figure 15:
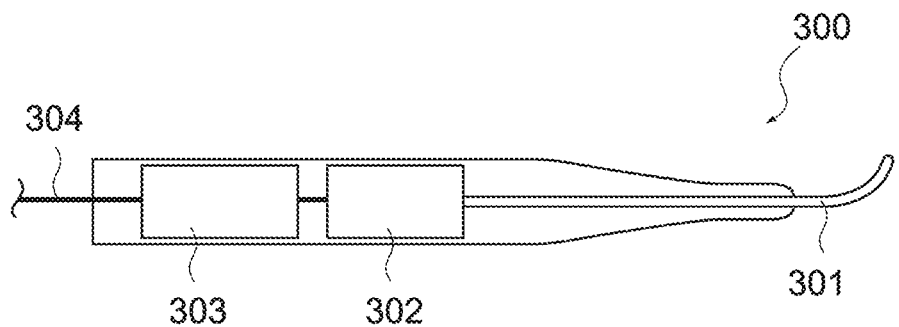
FIG. 15 is a schematic view showing an IVUS of an ultrasonic array oscillator in a comparative embodiment.

FIG. 15 is a schematic view showing an IVUS 300 having the related-art structure. As shown in FIG. 15, the IVUS 300 includes a catheter 301, an array oscillator 302, a signal processing chip 303, and a wiring line 304. Vascular walls are irradiated with the ultrasonic waves generated in the array oscillator 302 via the catheter 301 that is inserted into blood vessels, and the reflected waves enter into the array oscillator 302 via the catheter 301 and are detected. The detection signals are amplified by the signal processing chip 303 and are transmitted to a main body via the wiring line 304.

Thus, in the IVUS 300, the signal processing chip 303 is necessary to arrange separately from the array oscillator 302. The signal processing chip 303 inhibits bending of the IVUS 300, which makes the operation of the catheter 301 difficult.

Figure 16:
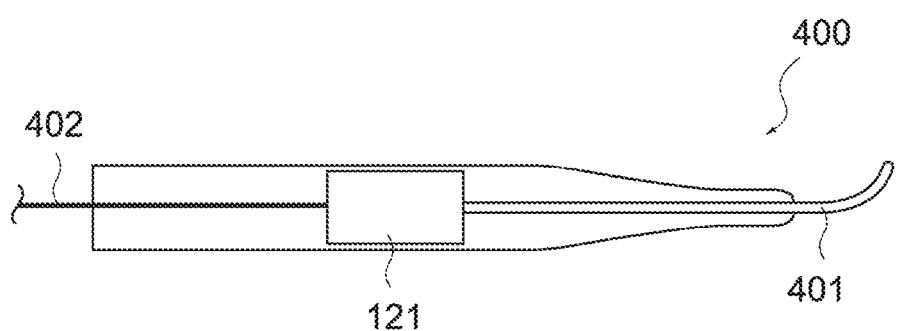
FIG. 16 is a schematic view showing an IVUS of the ultrasonic array oscillator according to an embodiment of the present technology.

FIG. 16 is a schematic view showing an IVUS 400 using the array oscillator 121 according to this embodiment. As shown in FIG. 16, the IVUS 400 includes a catheter 401, the array oscillator 121, and a wiring line 402. Vascular walls are irradiated with the ultrasonic waves generated by the array oscillator 121 via the catheter 401 that is inserted into blood vessels, and the reflected waves enter into the array oscillator 121 via the catheter 401 and are detected. The detection signals are amplified by the signal processing chips 140 included in the array oscillator 121 and are transmitted to a main body via the wiring line 402.

Since the array oscillator 121 includes the circuit chips 140, in the IVUS 400, there is no need to provide the signal processing chip in addition to the array oscillator 121. Thus, no signal processing chip inhibits bending of the IVUS 400, which makes the operation of the catheter 401 easy. Note that the IVUS 400 may include another signal processing chip unrelated to the impedance matching circuits. Even in this case, as no impedance matching circuits are necessary, it is possible to decrease the size of the signal processing chip.

[Co-mounting of Ultrasonic Oscillators and MEMS]

The oscillator module 120 according to this embodiment and MEMS modules including MEMS (Micro Electro Mechanical Systems) can be co-mounted.

Figure 17:
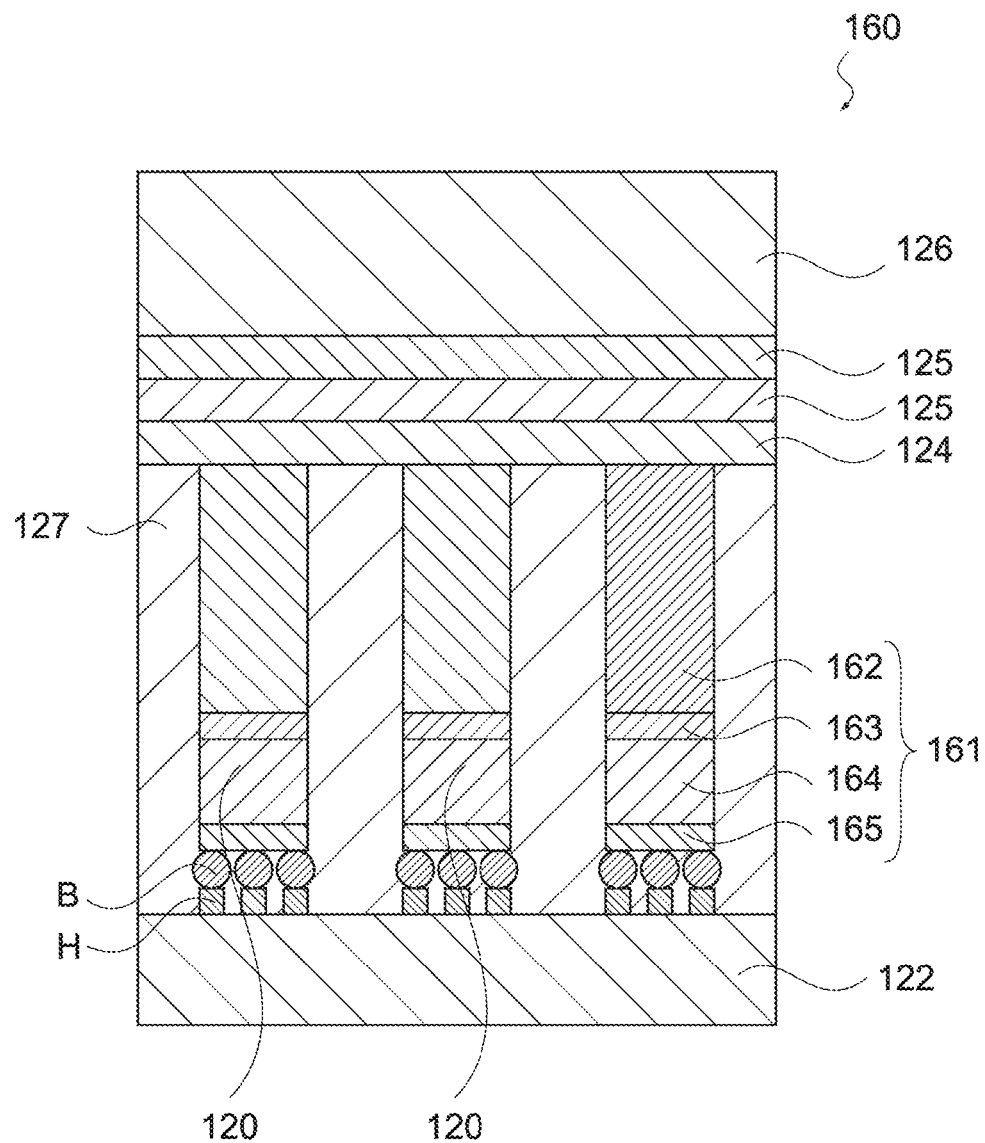
FIG. 17 is a cross-sectional view showing the ultrasonic array oscillator including the oscillator modules and the MEMS modules according to an embodiment of the present technology.

FIG. 17 is a schematic view showing an array oscillator 160 including oscillator modules and the MEMS modules co-mounted. As shown in FIG. 17, the array oscillator 160 includes the oscillator modules 120 and the MEMS modules 161. Other configurations of the array oscillator 160 are the same as those of the array oscillator 121.

Each MEMS module 161 includes an MEMS 162, a lower electrode layer 163, a backing layer 164, and a circuit chip 165. The MEMS 162 is an ultrasonic sensor formed by the MEMS. Specific configuration of the MEMS is not especially limited. The configurations of the lower electrode layer 163, the backing layer 164, and the circuit chip 165 are similar to those of the oscillator module 120. Note that the configuration of the MEMS module 161 is not limited to this, and may at least at least include MEMS 162.

Figure 18:
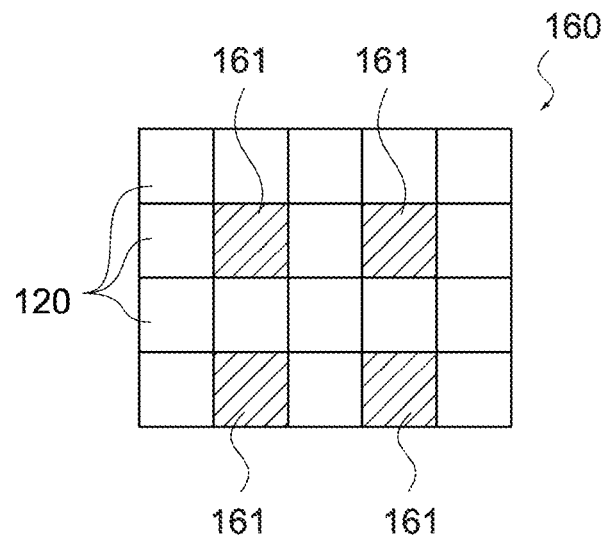
FIG. 18 is a schematic view showing an arrangement of the ultrasonic array oscillator.

FIG. 18 is a schematic view showing an arrangement of the oscillator modules 120 and the MEMS modules 161 of the array oscillator 160, and is viewed from the direction perpendicular to the substrate 122. As shown in FIG. 18, the oscillator modules 120 and the MEMS modules 161 are co-mounted on the substrate 122 to form the array. Note that the arrangement of the oscillator modules 120 and the MEMS modules 161 is not limited to that shown in FIG. 18.

With this configuration, the ultrasonic waves can be generated by using the oscillator modules 120 having great ultrasonic strength, and the reflected waves can be detected by using the MEMS modules 161 having high sensitivity. Thus, it is possible to improve an ultrasonic wave detection sensitivity.

Figure 19:
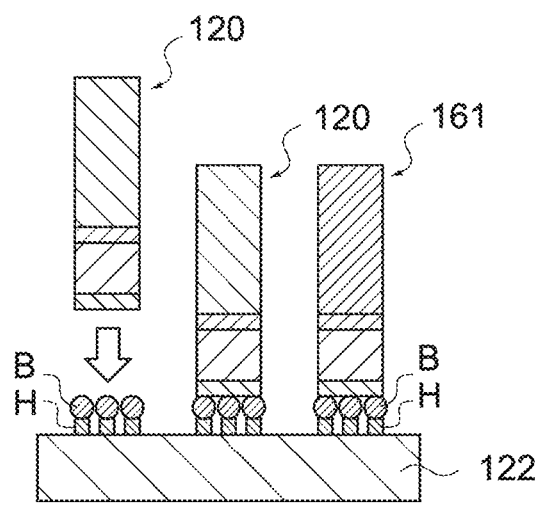
FIG. 19 is a schematic view showing a method of producing the ultrasonic array oscillator.

FIG. 19 is a schematic view showing a method of producing the array oscillator 160. As shown in FIG. 19, both of the oscillator modules 120 and the MEMS modules 161 can be mounted to the substrate 122 by using the pick-and-place method. After both the modules are mounted to the substrate 122, the filler 127, the upper electrode layer 124, the acoustic matching layer 125, and the acoustic lens 126 are formed. As a result, it is possible to produce the array oscillator 160 shown in FIG. 17, similar to the array oscillator 121.

[Co-mounting of Ultrasonic Oscillators and Optical Devices]

The oscillator modules 120 according to this embodiment and optical device modules including optical devices can be co-mounted.

Figure 20:
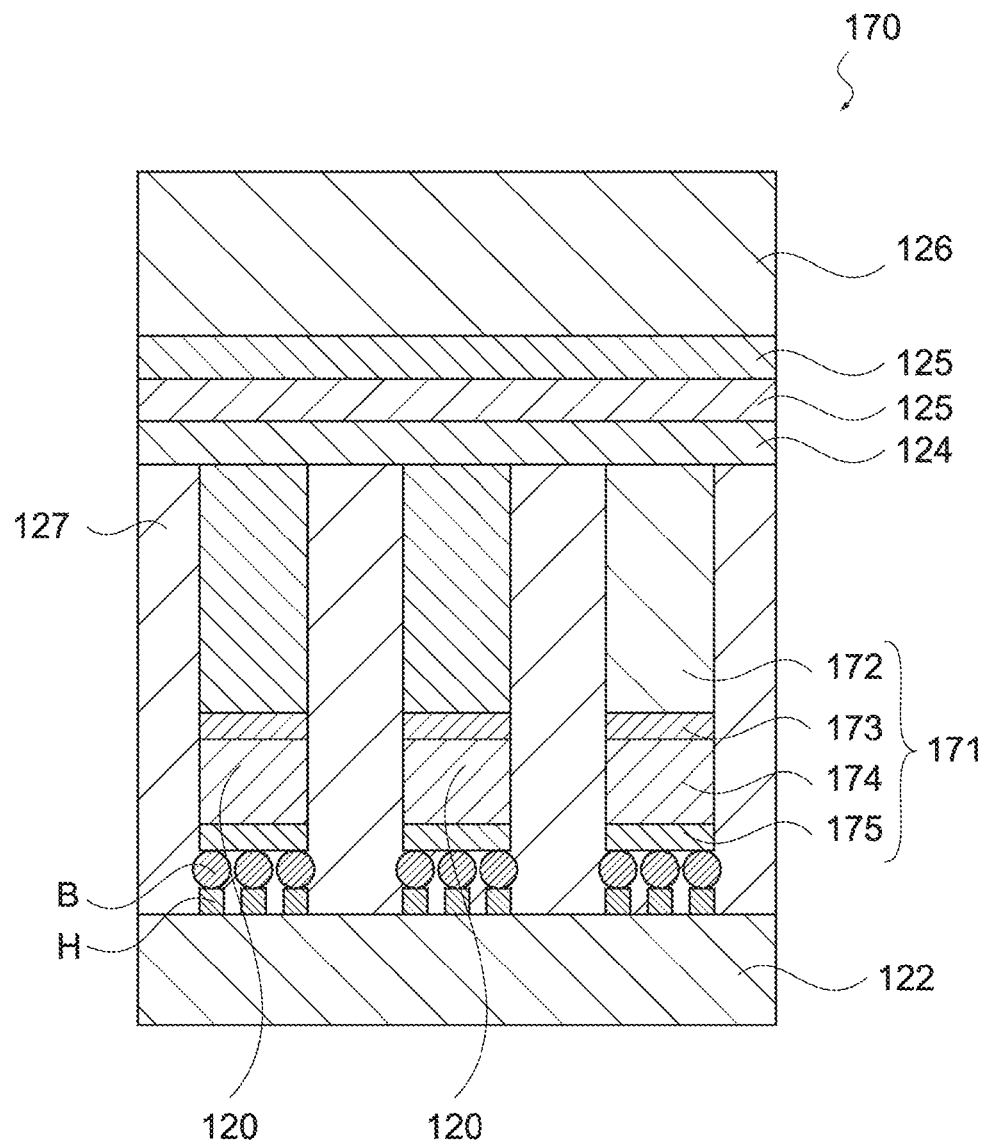
FIG. 20 is a cross-sectional view showing the ultrasonic array oscillator including the oscillator modules and optical device modules according to an embodiment of the present technology.

FIG. 20 is a schematic view showing an array oscillator 170 where the oscillator modules and the optical device modules are co-mounted. As shown in FIG. 20, the array oscillator 170 includes the oscillator modules 120 and optical device modules 171. Other configurations of the array oscillator 170 are the same as those of the array oscillator 121.

Each optical device module 171 includes an optical device 172, a lower electrode layer 173, a backing layer 174, and a circuit chip 175. The optical device 172 is a light-emitting device, and is a laser diode, for example. The configurations of the lower electrode layer 173, the backing layer 174, and the circuit chip 175 are the same as those of the oscillator module 120. Note that the optical device module 171 is not limited to this, and may at least include the optical device 172.

Figure 21:
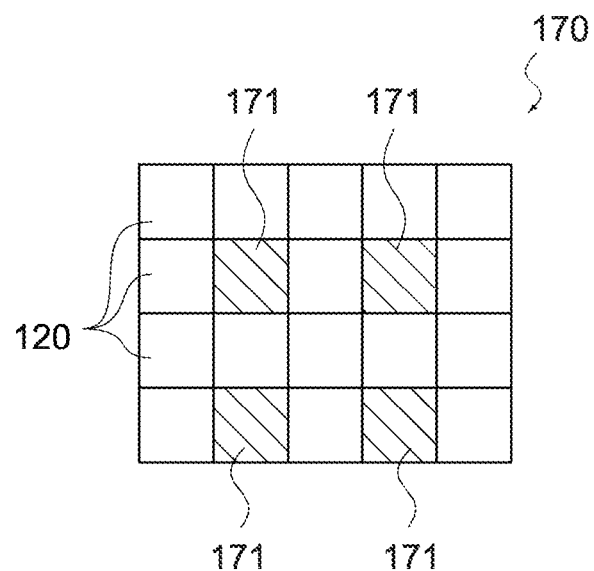
FIG. 21 is a schematic view showing an arrangement of the ultrasonic array oscillator.

FIG. 21 is a schematic view showing an arrangement of the oscillator modules 120 and the optical device modules 171 of the array oscillator 170, and is viewed from the direction perpendicular to the substrate 122. As shown in FIG. 21, the oscillator modules 120 and the optical device modules 171 are co-mounted on the substrate 122 to form the array. Note that the arrangement of the oscillator modules 120 and the optical device modules 171 is not limited to that shown in FIG. 21.

With this configuration, it is possible to execute light ultrasonic imaging, in which the object to be diagnosed is irradiated with light generated by the optical device modules 171 and the oscillator modules 120 detect the generated heat to thereby perform imaging.

In the related art, it is necessary to separately prepare a light-emitting apparatus including optical devices and an acoustic apparatus including acoustic devices for light ultrasonic imaging. According to the present technology, the ultrasonic oscillators 130 and the optical devices 172 can be formed as an array, and it is possible to perform light ultrasonic imaging with a single ultrasonic probe.

Figure 22:
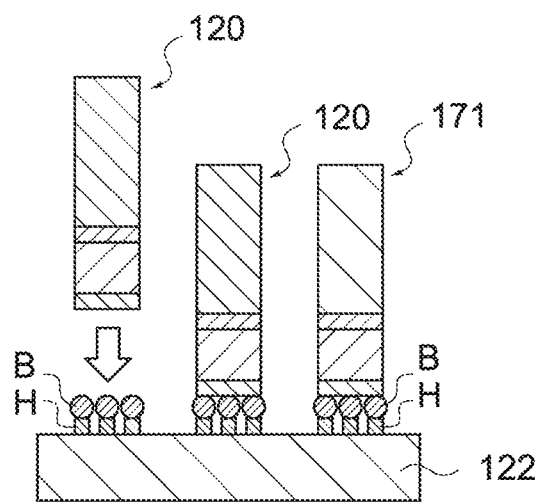
FIG. 22 is a schematic view showing a method of producing the ultrasonic array oscillator.

FIG. 22 is a schematic view showing a method of producing an array oscillator 170. As shown in FIG. 22, both of the oscillator modules 120 and the optical device modules 171 can be mounted to the substrate 122 by using the pick-and-place method. After both the modules are mounted to the substrate 122, the filler 127, the upper electrode layer 124, the acoustic matching layer 125, and the acoustic lens 126 are formed. As a result, it is possible to produce the array oscillator 170 shown in FIG. 20, similar to the array oscillator 121.

Note that the array oscillator 170 can include the above-described MEMS modules 161 in place of the oscillator modules 120. Further, the array oscillator 170 can include three types of modules, i.e., the oscillator modules 120, the MEMS modules 161, and the optical device modules 171, as an array.

Other than the array oscillator 160 and the array oscillator 170, any devices, which can be mounted by using the pick-and-place method, can be co-mounted together with the oscillator modules 120 and can be arrayed together with the oscillator modules 120.

The present technology may also have the following configurations.

(1) An ultrasonic array oscillator, including:
  ultrasonic oscillators that form an array; and
  semiconductor chips bonded to the respective ultrasonic oscillators that form impedance matching circuits.

(2) The ultrasonic array oscillator according to (1), in which
  each of the impedance matching circuits includes an amplifier and a TR (transmit-receive) switch.

(3) The ultrasonic array oscillator according to (1), in which
  each of the semiconductor chips includes a first semiconductor chip including the amplifier and a second semiconductor chip including the TR switch.

(4) The ultrasonic array oscillator according to according to any one of (1) to (3), in which
  each of the semiconductor chips is an SOI (Silicon on Insulator) chip.

(5) The ultrasonic array oscillator according to according to any one of (1) to (4), in which
  the ultrasonic oscillators include first ultrasonic oscillators each having a first frequency as a center frequency of oscillation and second ultrasonic oscillators each having a second frequency different from the first frequency as a center frequency of oscillation.

(6) The ultrasonic array oscillator according to according to any one of (1) to (5), further including:
  MEMS (Micro Electro Mechanical Systems), the MEMS and the ultrasonic oscillators forming the array.

(7) The ultrasonic array oscillator according to according to any one of (1) to (6), further including:
  optical devices, the optical devices and the ultrasonic oscillators forming the array.

(8) A method of producing an ultrasonic array oscillator, including:
  mounting ultrasonic oscillators, to which semiconductor chips that form impedance matching circuits are bonded, by using a pick-and-place method.

(9) The method of producing the ultrasonic array oscillator according to according to (8), in which
  the ultrasonic oscillators include first ultrasonic oscillators each having a first frequency as a center frequency of oscillation and second ultrasonic oscillators each having a second frequency different from the first frequency as a center frequency of oscillation.

(10) The method of producing the ultrasonic array oscillator according to according to (8) or (9), in which
  the mounting step includes mounting the ultrasonic oscillators and MEMS (Micro Electro Mechanical Systems) by using the pick-and-place method.

(11) The method of producing the ultrasonic array oscillator according to any one of (8) to (10), in which
  the mounting step includes mounting the ultrasonic oscillators and optical devices by using the pick-and-place method.

(12) An ultrasonic probe, including:
  an ultrasonic array oscillator including ultrasonic oscillators that form an array, and semiconductor chips bonded to respective of the ultrasonic oscillators that form impedance matching circuits.

(13) An ultrasonic diagnostic apparatus, including:
  an ultrasonic probe including an ultrasonic array oscillator, the ultrasonic array oscillator including ultrasonic oscillators that form an array, and semiconductor chips bonded to respective of the ultrasonic oscillators that form impedance matching circuits; and
  a main body to which the ultrasonic probe is connected, the main body supplying the ultrasonic array oscillator with a drive signal and generating an ultrasonic image on the basis of a detection signal output from the ultrasonic array oscillator.

REFERENCE SIGNS LIST

1 ultrasonic diagnostic apparatus
11 main body
12 ultrasonic probe
120 oscillator module
121 array oscillator
122 substrate
123 oscillator layer
124 upper electrode layer
125 acoustic matching layer
126 acoustic lens
127 filler
130 ultrasonic oscillator
131 piezoelectric layer
132 lower electrode layer
133 backing layer
160 array oscillator
161 MEMS module
170 array oscillator
171 optical device module

The invention claimed is:

1. An ultrasonic array oscillator, comprising:
  a plurality of ultrasonic oscillators in an array; and
  a plurality of semiconductor chips, wherein
    each semiconductor chip of the plurality of semiconductor chips is bonded to a respective ultrasonic oscillator of the plurality of ultrasonic oscillators,
    each semiconductor chip, bonded to the respective ultrasonic oscillator, comprises an impedance matching circuit, and
    a size of each semiconductor chip is smaller than a size of a bottom surface of the respective ultrasonic oscillator.

2. The ultrasonic array oscillator according to claim 1, wherein the impedance matching circuit includes an amplifier and a transmit-receive (TR) switch.

3. The ultrasonic array oscillator according to claim 2, wherein each semiconductor chip includes a first semiconductor chip including the amplifier and a second semiconductor chip including the TR switch.

4. The ultrasonic array oscillator according to claim 1, wherein each semiconductor chip is a Silicon on Insulator (SOI) chip.

5. The ultrasonic array oscillator according to claim 1, wherein
the plurality of ultrasonic oscillators includes a plurality of first ultrasonic oscillators and a plurality of second ultrasonic oscillators,
each first ultrasonic oscillator of the plurality of first ultrasonic oscillators has a first frequency as a first center frequency of oscillation, and
each second ultrasonic oscillator of the plurality of second ultrasonic oscillators has a second frequency different from the first frequency as a second center frequency of oscillation.

6. The ultrasonic array oscillator according to claim 1, further comprising:
Micro Electro Mechanical Systems (MEMS),
wherein the MEMS and the plurality of ultrasonic oscillators form the array.

7. The ultrasonic array oscillator according to claim 1, further comprising:
a plurality of optical devices,
wherein the plurality of optical devices and the plurality of ultrasonic oscillators form the array.

8. A method of producing an ultrasonic array oscillator, comprising:
mounting a plurality of ultrasonic oscillators by a pick-and-place method; and
bonding a plurality of semiconductor chips to the plurality of ultrasonic oscillators, wherein
each semiconductor chip of the plurality of semiconductor chips comprises an impedance matching circuit, and
a size of each semiconductor chip is smaller than a size of a bottom surface of an ultrasonic oscillator of the plurality of ultrasonic oscillators.

9. The method of producing the ultrasonic array oscillator according to claim 8, wherein
the plurality of ultrasonic oscillators includes a plurality of first ultrasonic oscillators and a plurality of second ultrasonic oscillators,
each first ultrasonic oscillator of the plurality of first ultrasonic oscillators has a first frequency as a first center frequency of oscillation, and
each second ultrasonic oscillator of the plurality of second ultrasonic oscillators has a second frequency different from the first frequency as a second center frequency of oscillation.

10. The method of producing the ultrasonic array oscillator according to claim 8, wherein the mounting includes mounting the plurality of ultrasonic oscillators and Micro Electro Mechanical Systems (MEMS) by the pick-and-place method.

11. The method of producing the ultrasonic array oscillator according to claim 8, wherein the mounting includes mounting the plurality of ultrasonic oscillators and a plurality of optical devices by the pick-and-place method.

12. An ultrasonic probe, comprising:
an ultrasonic array oscillator including a plurality of ultrasonic oscillators in an array; and
a plurality of semiconductor chips, wherein
each semiconductor chip of the plurality of semiconductor chips is bonded to a respective ultrasonic oscillator of the plurality of ultrasonic oscillators,
each semiconductor chip, bonded to the respective ultrasonic oscillator, comprises an impedance matching circuit, and
a size of each semiconductor chip is smaller than a size of a bottom surface of the respective ultrasonic oscillator.

13. An ultrasonic diagnostic apparatus, comprising:
an ultrasonic probe including an ultrasonic array oscillator,
wherein the ultrasonic array oscillator includes:
a plurality of ultrasonic oscillators in an array, and
a plurality of semiconductor chips, wherein
each semiconductor chip of the plurality of semiconductor chips is bonded to a respective ultrasonic oscillator of the plurality of ultrasonic oscillators,
each semiconductor chip, bonded to the respective ultrasonic oscillator, comprises an impedance matching circuit, and
a size of each semiconductor chip is smaller than a size of a bottom surface of the respective ultrasonic oscillator; and
a main body connected to the ultrasonic probe, wherein the main body is configured to:
supply the ultrasonic array oscillator with a drive signal; and
generate an ultrasonic image based on a detection signal output from the ultrasonic array oscillator.

* * * * *